United States Patent
Makris et al.

[11] Patent Number: 5,941,705
[45] Date of Patent: Aug. 24, 1999

[54] MANUAL DRIVE ENDODONTIC HANDPIECE

[75] Inventors: Georghios Makris, West Orange; Frank De Jackmo, Nutley, both of N.J.

[73] Assignee: Odontal Associates, Nutley, N.J.

[21] Appl. No.: 08/999,463

[22] Filed: Dec. 29, 1997

[51] Int. Cl.$^6$ ........................................................ A61C 3/00
[52] U.S. Cl. .................... 433/141; 433/114; 433/126; 433/133
[58] Field of Search ..................... 433/114, 126, 433/133, 127, 102, 141, 125

[56] References Cited

U.S. PATENT DOCUMENTS

| | | |
|---|---|---|
| Re. 7,452 | 8/1877 | Black . |
| 197,261 | 11/1877 | Finney . |
| 365,098 | 6/1887 | Register . |
| 389,796 | 9/1888 | Doriot . |
| 397,169 | 2/1889 | Campbell . |
| 408,439 | 8/1889 | Sheffield . |
| 622,467 | 4/1899 | Hermany . |
| 713,103 | 11/1902 | Hurlbut . |
| 797,106 | 8/1905 | Gray ............................... 433/141 |
| 873,100 | 12/1907 | Skalstad . |
| 937,126 | 10/1909 | Wentworth et al. . |
| 1,083,039 | 12/1913 | Wagar . |
| 1,216,375 | 2/1917 | Sved ................................. 433/133 |
| 3,727,313 | 4/1973 | Graham . |
| 4,234,308 | 11/1980 | Leonard ............................ 433/127 |
| 4,295,829 | 10/1981 | Martinelli et al. ................. 433/99 |
| 4,449,932 | 5/1984 | Lustig ............................... 433/126 |
| 4,911,639 | 3/1990 | Jacklich ............................ 43/102 |
| 5,020,994 | 6/1991 | Huang .............................. 433/126 |
| 5,529,495 | 6/1996 | Edwards ........................... 433/112 |
| 5,639,236 | 6/1997 | Martin .............................. 433/131 |

OTHER PUBLICATIONS

Product Catalog, Nobelcare AB, 1996, Special Equipment and Torque Driver Set shown at p.52.
Advertisement for Tri Auto–ZX, for J. Morita USA Inc., Aug., 1997.

*Primary Examiner*—John J. Wilson
*Attorney, Agent, or Firm*—David S. Jacobson

[57] ABSTRACT

A manual drive endodontic handpiece includes a housing having proximal end and a distal end provided with an angle head which receives a dental tool. A drive shaft extends through the housing and is coupled to a manual driver such that rotational movement of the manual driver causes rotational movement of the shaft. A pinion gear is provided at the distal end of the drive shaft and enters into the angle head. Rotation of the manual driver relative to the housing causes rotational movement of the pinion gear at the distal end of the shaft. A dental tool provided in the angle head has a head that includes a pinion gear which meshes with the pinion gear at the distal end of the shaft and is rotated by rotational movement of the pinion gear at the distal end of the shaft. According to one embodiment, the housing is provided with windows through which the manual driver may be directly rotated. According to another embodiment, an offset manual driver in conjunction with an axial driver permit manual rotation of the drive shaft. A spring is provided between the driver and drive shaft and biases the pinion gear at the distal end of the shaft into the angle head. Means are provided for moving the shaft against the bias of the spring to retract the pinion gear from the angle head and to permit a dental tool to be inserted in and removed from the angle head.

18 Claims, 4 Drawing Sheets

MANUAL DRIVE ENDODONTIC HANDPIECE

BACKGROUND OF THE INVENTION

1. Field of the Invention

This invention relates broadly to dental instruments. More particularly, this invention relates to endodontic handpieces, and especially handpieces adapted for performing root canal procedures.

2. State of the Art

The pulp filled cavity in the root of the tooth is known as the root canal. When the pulp and dentin on the root canal wall become infected, the pulp and dentin must be removed due to the severe pain the infection causes the patient. In addition to cleaning the canal of the infected dentin and pulp, the canal must be shaped to properly receive obturating material. The procedure for removing the pulp and infected dentin and shaping the canal is called a root canal procedure.

Shaping the root canal is a difficult task for even a skilled dentist as the root canal has narrow and tortuous curves. Moreover, the canals are normally less than a millimeter in diameter. It is therefore difficult to shape the canals to receive obturating material.

One method of shaping the root canal is for the dentist to hold a small cylindrical file (or reamer) in his fingers and to manually maneuver the file into the root canal; i.e., to rotate the file and to also move the file in an up and down motion such that the file enters the canal. By holding the file in his or her hand the dentist receives a high degree of tactile feedback regarding resistance of the file to entry into the canal. Resistance felt by the fingers of the dentist prompts the dentist to adjust the angle, motion, and force with which the file is moved into the canal. It will be appreciated that because of the size of the canal, the files used in the root canal procedure must also be of very small dimensions. If the narrow file is subject to excessive resistance, the file can break, leaving a broken portion in the canal and thereby complicating the root canal procedure with an additional procedure to recover the file portion. Therefore, high tactile feedback of resistance is extremely important.

However, the use of hand-held files is difficult for both the dentist and the patient. When the dentist uses a hand-held file, he or she must operate with his or her fingers within the mouth of the patient. This is uncomfortable to the dentist and patient. Moreover, the rotational movement by the fingers causes fatigue to the dentist. Furthermore, placement of the fingers of the dentist within the mouth of the patient to operate the file prevents the dentist from seeing the progress of the procedure, as the fingers block the view of the dentist.

As a result, a power driven endodontic handpiece is generally used to rotate the file, with the dentist providing up and down translation of the file by manipulation of the handpiece. A power driven endodontic handpiece generally includes an elongate shank (or handle) grippable in the hand of the dentist, a distal angle portion (angle head) which is oriented orthogonal to the shank and into which the non-operational end of files, drills, burs, and other tools are interchangeably received, and a proximal drive mechanism coupled to a power supply, e.g., AC power, a battery, or compressed air, to automatically operate the drive mechanism and rotate a dental tool secured in an angle head. As a result, root canal procedures can be performed with a powered endodontic handpiece fit with a file, rather than by manual manipulation by the dentist of a file. Moving the file via an endodontic handpiece does have certain advantages over manipulation of a file with fingers uncomfortably positioned within the mouth of a patient. The fingers of the dentist are not subject to certain stresses and, as a result, do not typically suffer from fatigue. Second, because the angle head is relatively smaller than the fingers of the dentist, the mouth of the patient is also not required to be forced open to the same degree as would otherwise be necessary. Furthermore, the size of the angle head permits the dentist to view the progress of the procedure.

However, root canal performed with a power driven endodontic handpiece also has several drawbacks. Foremost, the dentist does not receive tactile feedback when operating a powered handpiece. As a result, undesirable stresses upon the file that otherwise would be perceived by the fingertips of the dentist are not so perceived, and the file is more likely to fracture. Furthermore, due to the speeds at which powered handpieces typically operate (300 rpm or higher), the likelihood of error and ledging, i.e., the creation of an undesirable ledge at the entrance to the root canal, is increased.

Moreover, while it is fairly easy to use different dental tools when the dental tools are manipulated in the fingers (i.e., to move from a file of one size to a relatively smaller file requires nothing more than placing down the larger file and picking up the smaller file), changing from one dental tool to another with an endodontic handpiece can be relatively more complicated. In order to clearly explain the potential complications, it must first be appreciated that endodontic handpieces are provided with various coupling means to engage the dental tool to the drive mechanism. Such coupling means typically require a latching mechanism or a frictional collet mechanism. Also such coupling means add both to manufacturing complexity and the size of the angle head. Furthermore, in the prior art, the mechanisms that provide for acceptable coupling of the dental tool in the angle head have created limitations on the size of dental tool which may be used by the endodontic handpiece and have caused excessive complexity with respect to the interchange from one dental tool to another.

As an example, U.S. Pat. No. 4,449,932 to Lustig discloses an endodontic handpiece for driving a dental tool having gear teeth at one end and an operational end (e.g., a file) opposite the gear teeth. The handpiece includes a small access opening orthogonally through its distal end, thereby forming the angle head. In order that the dental tool be inserted and secured in the angle head, the dental tool must be laboriously and precisely guided though one end of the small opening and then pulled through the other end. In the case of an endodontic file, this is the equivalent of threading a needle. In addition, the required technique increases the hazard of the finger of the practitioner being punctured. Furthermore, a cover must be locked over the distal end of the handpiece to lock the dental tool in position (i.e., so that the dental tool is not pushed back through the small access opening), thereby increasing the bulk of the distal end of the handpiece. Moreover, this arrangement requires that dental tools have a operational end smaller than the gear-toothed end, thereby limiting the size, design, and types of dental tools that can be used with the handpiece.

More significantly, during the root canal procedure, the file preferably is temporarily retained in the canal for radiographic evaluation of the procedure. Thus, ease of controlled handpiece separation from the file while the file is located within the root canal is of extreme importance. This is impossible with the Lustig device and extremely difficult with existing file locking mechanisms.

SUMMARY OF THE INVENTION

It is therefore an object of the invention to provide a manually operable dental handpiece.

It is another object of the invention to provide an endodontic handpiece which is optimized for use during root canal procedures in that it provides a dentist using the handpiece with tactile feedback on the resistance encountered by a dental tool secured in the endodontic handpiece.

It is a further object of the invention to provide an endodontic handpiece in which dental tools can easily be secured within and from which dental tools can easily be removed.

It is an additional object of the invention to provide an endodontic handpiece that can be comfortably used by a dentist in single-handed operation.

It is also an object of the invention to provide an endodontic handpiece that can easily be disassembled for servicing.

It is yet another object of the invention to provide an endodontic handpiece that is relatively easy to manufacture.

In accord with these objects, which will be discussed in detail below, a manual drive endodontic handpiece is provided. The endodontic handpiece generally includes a hollow, cylindrical housing having proximal and distal ends, the distal end being provided with an angle head which receives a dental tool, a driver having proximal and distal ends and extending through the housing, a drive shaft also extending through the housing and having proximal and distal ends, the proximal end of the drive shaft being coupled to the distal end of the driver such that rotational movement of the driver causes rotational movement of the drive shaft, and means for manually rotating the driver relative to the housing. Preferably a pinion gear is provided at the distal end of the drive shaft and enters into an opening of the angle head. Rotation of the driver relative to the housing causes rotational movement of the pinion gear. A dental tool secured in the opening of the angle head and having a head that includes a pinion gear which meshes with the pinion gear at the distal end of the drive shaft is rotated by the rotational movement of the pinion gear at the distal end of the drive shaft.

According to a first embodiment of the invention, one or more windows are provided in the wall of the housing so that the driver may be manually rotated through the windows. According to a second embodiment of the invention, the driver includes an axial drive member and an offset drive member preferably oriented perpendicular to the axial drive member. A distal end of the offset drive member is provided with a pinion gear that meshes with a pinion gear provided at a proximal end of the axial drive member. The axial driver is coupled to the drive shaft. The proximal end of the offset drive member extends out of the housing to permit manual rotation of the offset drive member by the dentist.

According to a preferred aspect of the invention, a spring is provided between the driver and drive shaft to urge the pinion gear at the distal end of the drive shaft into the opening of the angle head. Means for moving the drive shaft against the bias of the spring and relative to both the driver and the housing is provided. The drive shaft is thereby movable such that pinion gear is at least partially retractable out of the opening of the angle head to permit easy insertion and replacement of a variety of dental tools. It will be further appreciated that as only the head of the dental tool is inserted into the angle head, the size of the operational end (the reaming, filing, cutting, buffing, etc. end) of the dental tool is independent of the head size of the dental tool. According to another preferred aspect of the invention, the housing is comprised of at least two detachably coupled components which, when desired, easily decouple to permit access to the interior of the housing to permit servicing, should any service to the handpiece be required.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
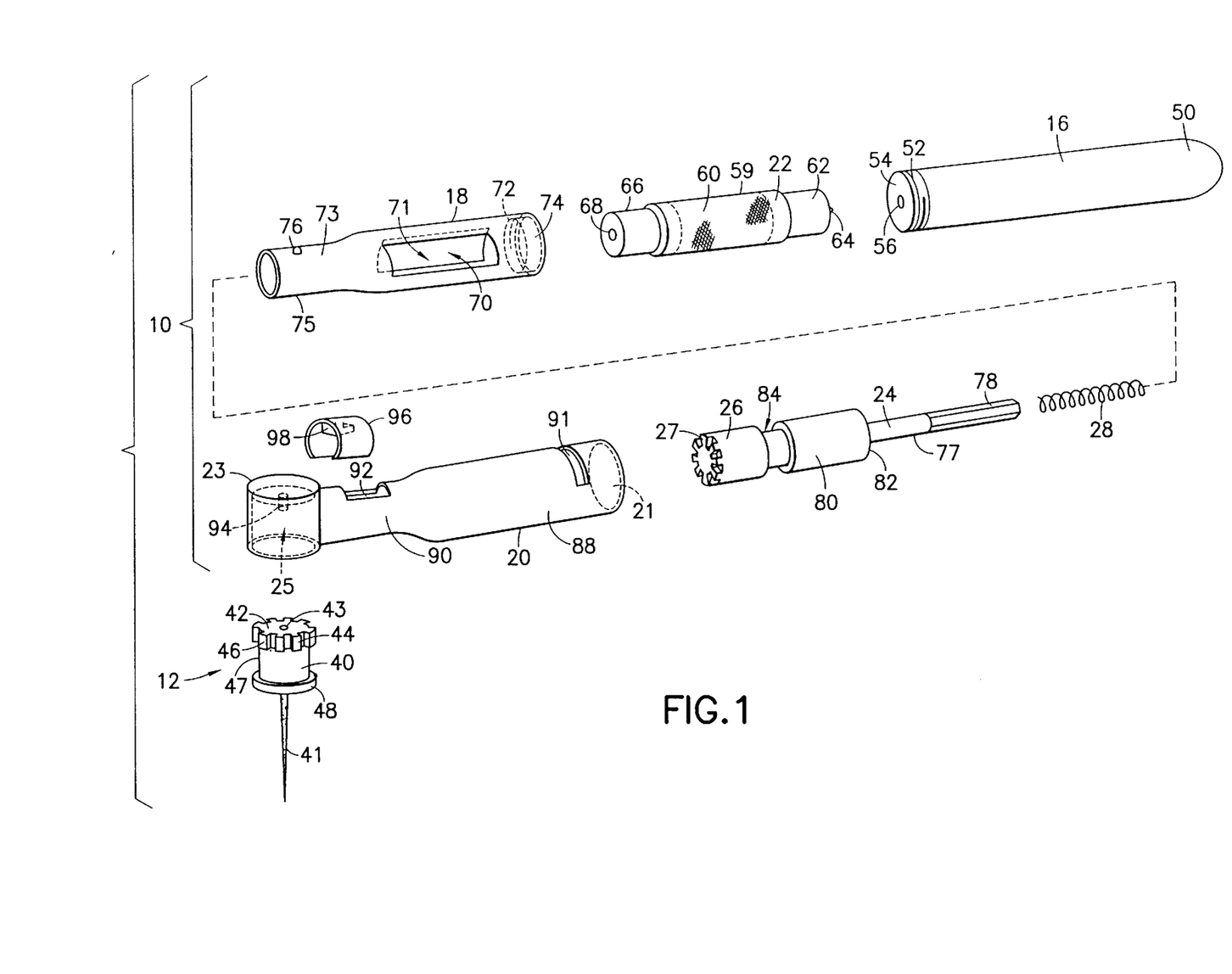
FIG. 1 is an exploded perspective view of a first embodiment of a manual drive endodontic handpiece according to the invention with a dental tool.
Figures 2, 3:
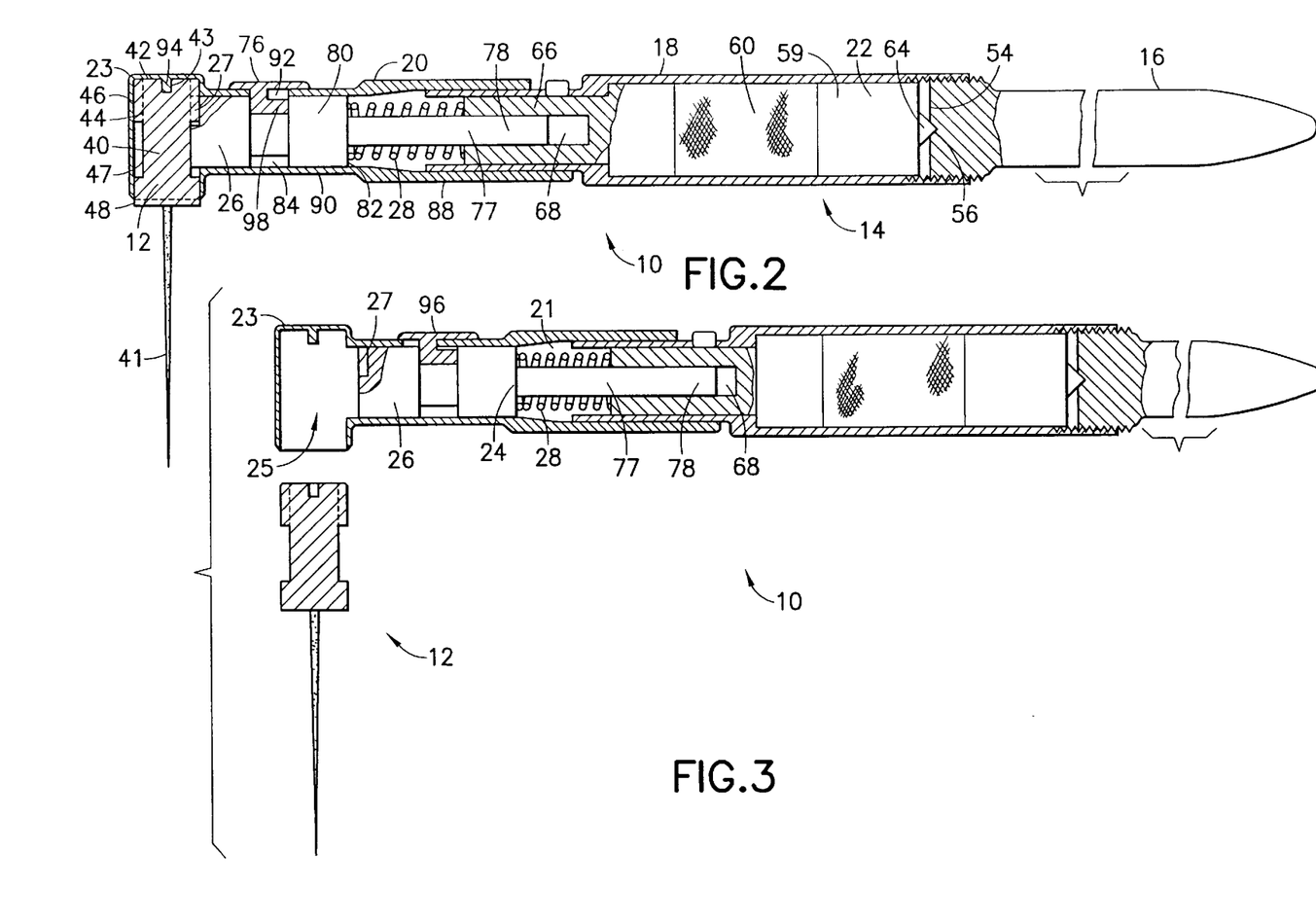
FIG. 2 is partial view of the manual drive endodontic handpiece of FIG. 1 with a dental tool held within the handpiece.
FIG. 3 is a partial view of the manual drive endodontic handpiece of FIG. 1 showing a dental tool released from the handpiece.

Turning now to FIG. 1, a manual drive endodontic handpiece 10 according to the invention and dental tool 12 insertable into the handpiece 10 are shown. The manual drive endodontic handpiece 10 generally includes a proximal cylindrical housing 14 comprised of a shank (handle) 16, a hollow tubular member 18, and an angle member 20, and, within the housing 14, a driving member (driver) 22, a drive shaft 24, and a compression spring 28. Turning now to FIG. 2, the shank 16 is coupled to the tubular member 18 and the tubular member 18 is coupled to the angle member 20. The driver 22 is substantially provided within the tubular member 18 and the shaft 24 is substantially provided within the angle member 20, with the compression spring 28 urging the driver 22 and shaft 24 away from each other. The various components of the endodontic handpiece are preferably made from stainless steel.

Referring now to both FIGS. 1 and 2, the shank 16 is provided with a rounded or tapered proximal end 50, external threads 52 adjacent its distal end 54, and an axial depression 56 in its distal end. The driver 22 is provided with a central portion 59, a proximal end 62, and a distal end 66. The central portion 59 of the driver 22 includes finger engagement means 60, such as knurls. The proximal end 62 of the driver 22 is provided with a protuberance 64 able to be at least partially received in the depression 56 in the shank 16. The distal end 66 of the driver 22 is provided with a bore 68 having a non-circular cross section, e.g., a hexagonal cross section.

The tubular member 18 is provided with preferably two lateral, longitudinal windows 70, 71, internal threads 72 adjacent its proximal end 74, and a preferably narrowed distal end 75 preferably provided with an external locking nub 76. The driver 22 is received within the tubular member 18 such that the finger engagement means 60 are manipulable through the windows 70, 71 of the tubular member 18 and further such that the distal end 66 of the driver resides in the narrowed distal end 73 of the tubular member. The tubular member 18, with driver 22 within, is removably threadably coupled to the shank 16 via the external threads 52 and internal threads 72 on the shank and tubular member, respectively.

The drive shaft 24 includes an axle 77, a cylinder 80, and a gear portion 26 with gear teeth 27. The axle 77 has a proximal end 78 which is shaped to be received within the bore 68 of the driver and preferably has a similarly shaped non-circular cross-section to the bore; i.e., the proximal end 78 of the axle 77 and bore 68 have rotationally interfering cross-sections. The relatively larger cylindrical portion 80 of the drive shaft 24 has a proximal abutment wall 82, and is separated from the gear portion 26 by an annular groove (slot) 84. The distal end of the shaft 24 includes the gear portion 26 with distal face gear teeth 27 arranged in a pinion gear fashion. The proximal end 78 of the shaft 24 extends through the compression spring 28, and further partially enters into the bore 68 of the driver 22, such that the first pinion gear portion 26 and annular groove 84 of the shaft extend distally from the narrowed end 75 of the tubular member 18. The compression spring 28 urges the drive shaft 24 away from the driver 22.

The angle member 20 includes a proximal portion 88, a central portion 90, a first bore 21 extending substantially coaxial with the axis of the housing, and an angle head 23 partially defined by a second bore 25 angled relative to the first bore 21. The inner diameter of the proximal portion 88 of angle member 20 is substantially the same as the outer diameter of the narrowed distal portion 75 of the tubular member 18 (such that the two may form an interference fit). A central portion 90 of the angle member 20 preferably has a relatively smaller diameter than the proximal portion 88 and the angle head 23. The proximal portion 88 of the angle member 20 is provided with an L-shaped slot 91. The angle head 23 is preferably provided with an upper rotation pin 94.

In assembling the angle member 20 to the tubular member 18, the proximal portion 88 of the angle member 20 is pushed over the distal end 75 of the tubular member 18 such that the locking nub 76 enters the L-shaped slot 91. The angle member 20 is then rotated relative to the tubular member 18 to, in combination with the interference fit, removably lock the angle member to the tubular member. Conversely, by twisting the angle member 20 relative to the tubular member 18 and pulling the angle member and tubular member away from each other to overcome the interference fit, the angle member and tubular member may be disassembled.

According to a preferred aspect of the invention, the central portion 90 of the angle member 20 is provided with an upper window 92, and a tubular-segment-shaped release collar (button) 96 having a lower L-shaped catch 98. The release collar 96 is seated over the central portion 90. When the angle member 20 is locked to the tubular member 18, the first teeth 27 of the first pinion gear portion 26 of the drive shaft 24 enter into the angle head 23 and the annular groove 84 is generally located beneath the upper window 92, such that the L-shaped catch 98 enters into the window 92 and engages the drive shaft 24 at the annular groove 84.

Referring to FIG. 3, the release collar 96 may be manually moved proximally with a finger of a dentist to move proximally the first pinion gear portion 26 of the drive shaft 24, causing the compression spring 28 to be compressed between the abutment wall 82 and the distal end of the driver 22, and also causing the proximal end 78 of the axle 77 of the drive shaft 24 to extend further into the bore 68. The first teeth 27 of the first pinion gear portion 26 of the drive shaft 24 are thereby withdrawn from the angle head 23 to permit the insertion or removal of the dental tool 12 from the angle head 23.

Turning back to FIG. 1, the dental tool 12 for use with the endodontic handpiece includes a head portion 40 and an operational end 41, such as a file. The head portion 40 has an upper base 42 provided with a bore 43, a central portion 47 provided with second face gear teeth 46 which abut the upper base 42, and a lower base 48. The central portion with its second gear teeth 46 form a second pinion gear portion 44 which meshes with the first teeth 27 of the first gear portion 26. The upper and lower bases 42, 48 have substantially the same diameter and the central portion 47 has a constricted diameter relative to the upper and lower bases. Preferably, the length of the central portion; i.e., the distance between the upper base 42 and the lower base 48, is substantially equal to the diameter across the first gear teeth 27 of the first gear portion 26. The head portion 40 of the dental tool 12 is received into the second bore 25 of the angle head 23 such that the second gear portion 44 interlocks at preferably a ninety degree angle with the first gear portion 26 of the shaft 24; i.e., the first and second gear teeth 27, 46 are preferably oriented perpendicular to each other. When the dental tool 12 is received within the angle head 23, the bore 43 of the dental tool is seated over the rotation pin 94 in the angle head to stabilize the dental tool, as well as to provide reduced frictional torque support.

It will be appreciated that the manual drive endodontic handpiece 10 permits a dentist to hold the handpiece in his or her hand and use one or more fingers of the same hand (or, if desired, his or her other hand) to engage the finger engagement means 60 of the driver 22 to rotate the driver. Rotation of the driver, in turn, rotates the drive shaft 24, as the shaft is rotationally coupled to the driver as a result of the proximal end 78 of the drive shaft and the bore 68 in the driver having rotationally interfering non-circular cross-sections. Rotation of the drive shaft 24 causes the teeth 27 of the first pinion gear portion 26 to rotate about the rotational axis of the drive shaft and, in turn, to rotate the dental tool 12 provided in the angle head 23 about the rotational axis of the dental tool, which in the preferred embodiment is perpendicular to the rotational axis of the shaft.

The manual drive endodontic handpiece of the invention has several advantages over the prior art. First, the handpiece may be used to drive a dental tool from outside the mouth of a patient, thereby reducing fatigue for both patient and dentist. Second, this may be done without an expensive power drive mechanism in the handpiece. Third, and particularly with respect to performing a root canal procedure, the fingers of the hand of the dentist are able to receive feedback of resistance from the operational end of the dental tool (that is, the driver will be more difficult to manually rotate as the operational end of the dental tool encounters increased resistance), so that adjustments to the procedure can be made. As a result, breakage of the dental tool is prevented and, more importantly, damage to the mouth of the patient is prevented. Fourth, with the simple push of a button, the dental tool may easily be released from the angle head thereby permitting x-ray photographs of the dental tool within the root canal, manual operation of the dental tool via the fingers of the dentist without having to remove the dental tool from canal, or an easy interchange from one dental tool to another. Fifth, as operation of the handpiece may be performed with a single hand, the hand of the dentist not operating the handpiece is freed to perform other related activity. Sixth, as only the head of the dental tool is inserted into the angle head, the size of the operational end (the reaming, filing, cutting, buffing, etc. end) of the dental tool is independent of the head size. Seventh, the handpiece should not require regular maintenance. However, should maintenance of the handpiece be required, the few components of the handpiece easily come apart to reveal any problems and permit servicing.

Figure 4:
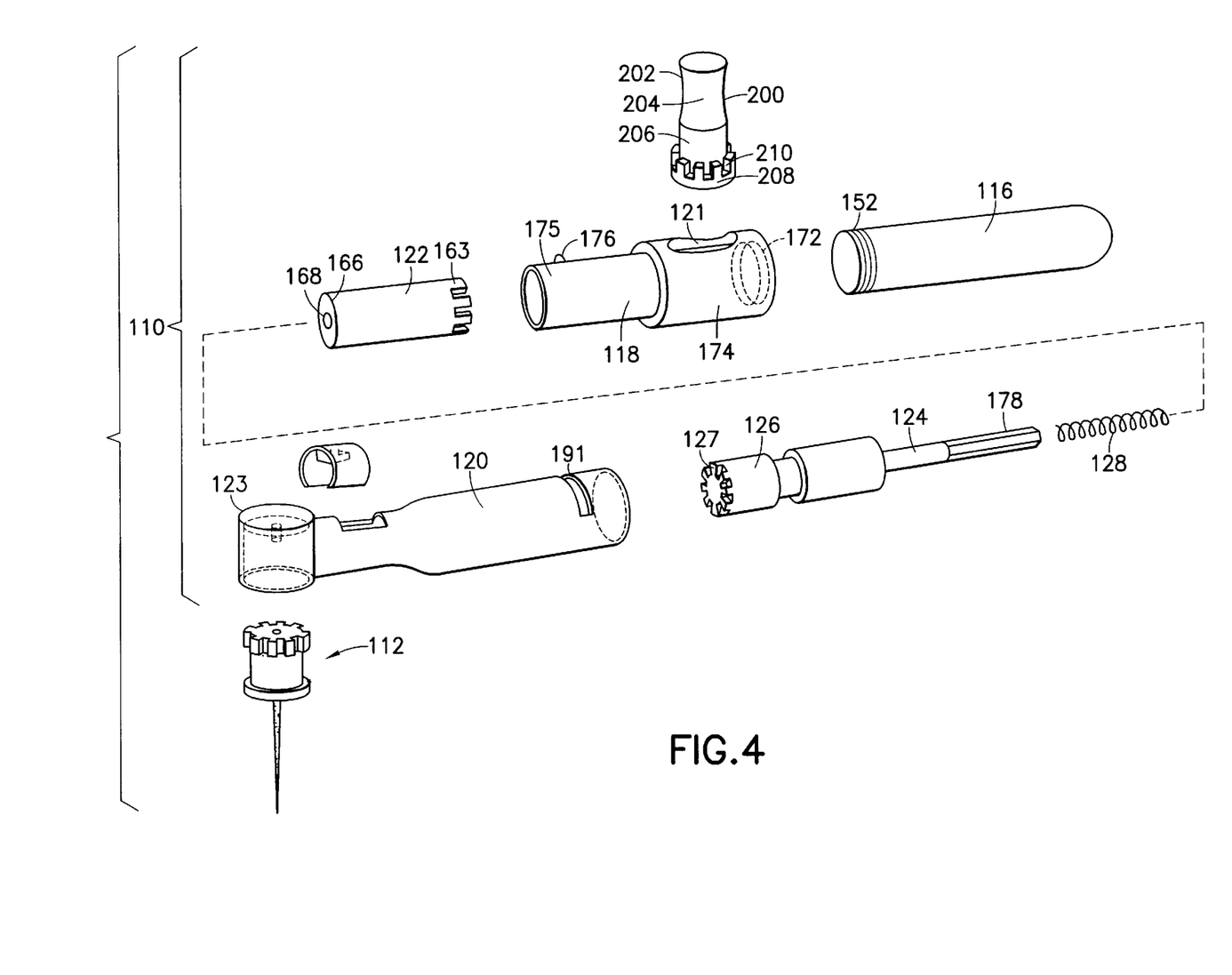
FIG. 4 is an exploded perspective view of a second embodiment of a manual drive endodontic handpiece according to the invention.
Figure 5:
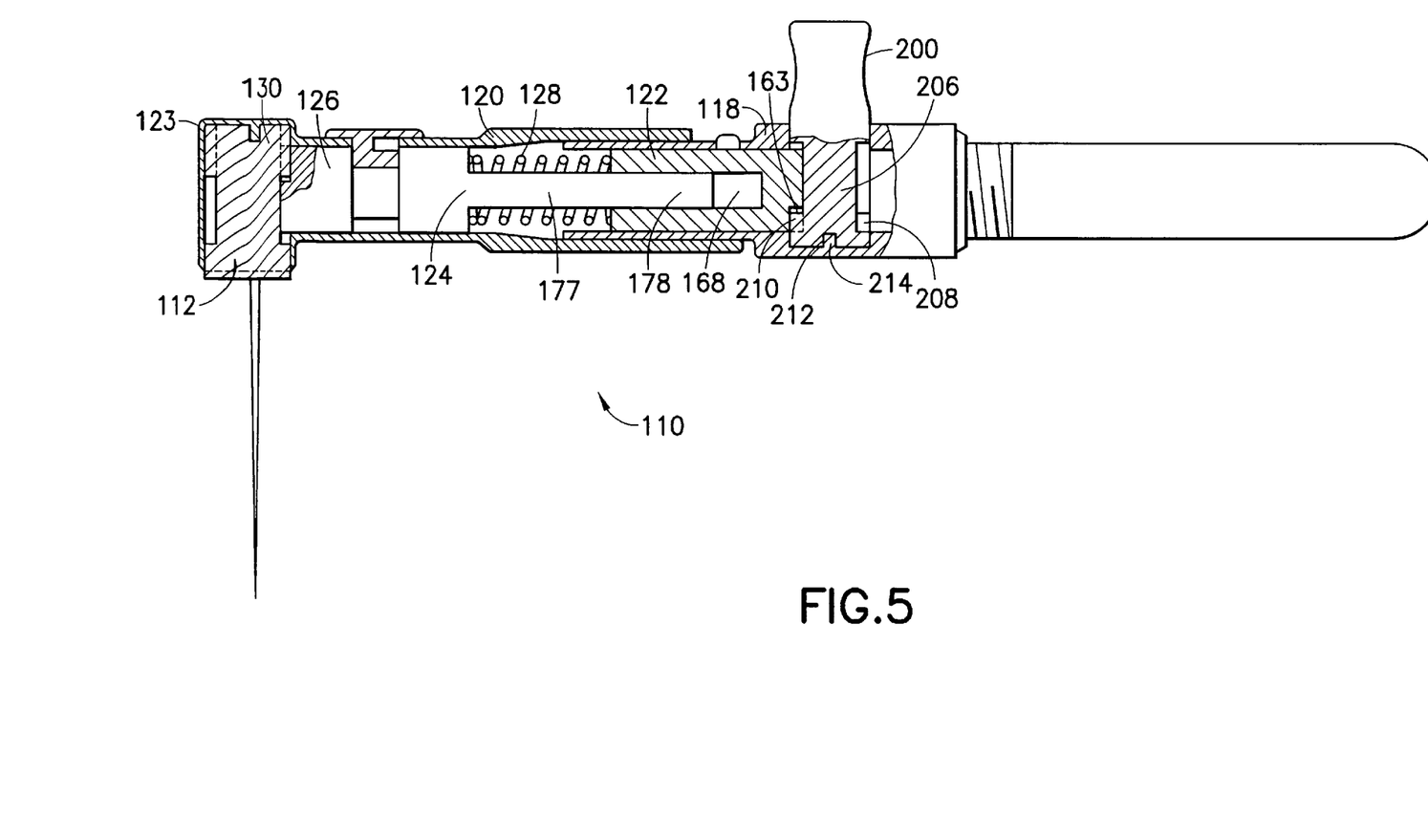
FIG. 5 is a partial view of the manual drive endodontic handpiece of FIG. 4 with a dental tool held within the handpiece.

Turning now to FIGS. 4 and 5, a second embodiment of the invention, substantially similar to the first embodiment (with like parts having numbers incremented by 100), is shown. According to a second embodiment of the invention, the endodontic handpiece 110 includes a shank 116, a tubular member 118, a driver having an axial drive member 122 and an offset drive member 200, and an angle member 120. The shank 116 has external distal threads 152. The tubular member includes a proximal portion 174 having a lateral opening 121 and internal threads 172 which mate with external threads 152 at the distal end of the shank 116, and a relatively smaller diametered distal portion 175 having a locking nub 176.

The offset manual drive member 200 extends through the lateral opening 121 of the tubular member 118. The offset drive member 200 includes a handle 202, preferably provided with a knurled surface 204, which remains external of the tubular member 118, a cylindrical body 206, a relatively larger cylindrical base 208, teeth 210 provided around the lower portion of the body 206 adjacent the base 208, and a bore 212 which stabilizes the offset drive member 200 over a rotation pin 214 on the interior floor of the tubular member 118. The axial drive member 122 is provided with proximal teeth 163 and, at its distal end 166, a bore 168 having a non-cylindrical cross-section. The proximal end of the axial drive member 122 extends through the distal portion 175 of the tubular member 118 such that the proximal teeth 163 engage the teeth 210 of the offset drive member 200.

The drive shaft 124 includes a distal first pinion gear portion 126 having proximal teeth 127 and an axle 177 with a proximal portion 178 having a non-circular cross-section. The proximal portion 178 of the axle 177 partially extends into the bore 168 of the axial drive member 122. A compression spring 128 is provided between the axial drive member 122 and the drive shaft 124 urging the axial drive member 122 and the drive shaft 124 away from each other. As a result, the first pinion gear portion 126 of the drive shaft 124 is biased into the angle head 123 and the proximal teeth 163 of the axial drive member 122 are forced into the teeth 210 of the offset drive member 200. The offset drive member 200 is thereby held from being withdrawn from the tubular member 118 of the handpiece unless the axial rotation driver is permitted to move distally; i.e., when the angle member and tubular member are disassembled as described above with respect to the first embodiment.

A combination of an interference fit and an L-shaped slot 191 in the angle member locking with locking nub 176 on the tubular member 118 removably couples the angle member 120 and tubular member 118 together, as described in above with respect to the first embodiment.

It will be appreciated that the rotation of the handle 202 of the offset drive member 200 about its axis (which is preferably perpendicular to the axial drive member 122) using one or more fingers of the dentist causes rotation of the drive shaft 124 about its axis of rotation (FIG. 4). The drive shaft 124, in turn, causes rotation of a dental tool 112 about another axis, preferably perpendicular to the axis of the axial driver 122. The first pinion gear portion 126 of the drive shaft 124 may be retracted from the angle head 123 for the insertion and removal of a dental tool 112, as also described above.

There have been described and illustrated herein embodiments of a manual drive endodontic handpiece. While particular embodiments of the invention have been described, it is not intended that the invention be limited thereto, as it is intended that the invention be as broad in scope as the art will allow and that the specification be read likewise. Thus, while particular manual drive means have been disclosed, it will be appreciated that other manual drive means may be used as well. For example, an Archimedes screw-type manual drive means, meshing pinion gears otherwise designed (e.g., with forty-five degree angled teeth), a universal joint manual drive means, a manual belt drive means, a drive spring, e.g., as disclosed in U.S. Pat. No. 5,529,495, and other drive means adaptable for manually driving an endodontic handpiece may also be used. Also, while the engagement means between the drive shaft and the dental tool has been described as being meshing teeth of respective pinion gears on each, it will be appreciated that the engagement means need not use gear teeth. For example, the engagement means may alternatively be a clutch system. Moreover, while it has been shown that rotation of the dental tool occurs about an axis substantially perpendicular to the longitudinal axis of the handpiece, it will be appreciated that the angle member and teeth of the pinion gears may be configured to rotate the dental tool about an axis that is not perpendicular to the longitudinal axis of the handpiece. Furthermore, while a particular type of release button for withdrawing the teeth of the first pinion gear portion from the angle head has been disclosed, it will be understood that other release means may also be used. Also, while the shaft and bore have been shown with a pentagonal cross section, other non-circular cross-sections, e.g., rectangular or pentagonal, can be used. Moreover, while the cross sections of the shaft and bore are described as being substantially the same, the cross sections of each may be different as long as the cross sections are rotationally interfering; e.g., the shaft may have a six-sided star-shaped cross-section, while the bore may be hexagonally shaped to receive the shaft. Furthermore, while a coiled compression spring is described as urging the first pinion gear portion of the drive shaft into the angle head, it will be appreciated that other resilient spring-like members may alternatively be used. In addition, while stainless steel is preferred for the manufacture of the endodontic handpiece, other materials including other metals and plastics may also be used. Furthermore, while in the first embodiment, the housing has been described as being comprised of a shank, a tubular member, and an angle member, it will be understood that the housing may be machined from a fewer or a greater number of pieces, and that the drive shaft and driver may also be made from one unitary member or a greater number of pieces. For example, where the shaft and driver are a singular component, a spring may be provided at the proximal end of the component to permit the shaft and driver component to be retracted from the angle head. Also, while various components have been described as being coupled together in particular ways, it will be appreciated that the components may be coupled in other ways. For example, where threaded couplings are shown, interference fits or snap fits may be used in the alternative. Also, while locking nub is preferably included on the distal portion of the tubular member, it will be appreciated that the locking nub is not required and that the interference fit will satisfactorily couple the angle member and tubular member together. Moreover, the handle may be configured to connect to standard and other commercially available angle head drivers in place of the described angle member. In addition, while the endodontic handpiece has been shown to include both a manual drive means and a retractable driver, it will be appreciated that the handpiece need not be provided with both of these preferred aspects. It will therefore be appreciated by those skilled in the art that yet other modifications could be made to the provided invention without deviating from its spirit and scope as so claimed.

What is claimed is:

1. An endodontic handpiece holdable in a hand of a dentist and manually operable using a single hand of the dentist, said handpiece for rotating a dental tool about a dental tool rotational axis, the dental tool having an engagement portion, said endodontic handpiece comprising:
   a) a housing having a first end including an angle head, a second end, an interior, and a longitudinal axis, said angle head having an opening angled relative to said longitudinal axis of said housing, and sized to receive the engagement portion of the dental tool;
   b) a drive shaft extending at least partially through said housing, said drive shaft having first and second ends and a rotational axis substantially parallel to said longitudinal axis;
   c) tool engagement means for engaging the engagement portion of the dental tool, said tool engagement means being coupled to said first end of said drive shaft and extending into said opening of said angle head of said housing; and
   d) a manual drive member provided with a finger engagement means, said manual drive member coupled to said drive shaft and located between said first and second ends of said housing for translating movement of at least one finger of the dentist into rotation of said drive shaft, said manual drive member having an axis of rotation substantially perpendicular to said rotational axis of said drive shaft and substantially provided in a plane extending through the rotational axis of the dental tool,
   wherein when said drive shaft is rotated about said rotational axis of said drive shaft, a dental tool received in said opening and having its engagement portion engaged by said tool engagement means is rotated about the dental tool rotational axis.

2. An endodontic handpiece according to claim 1, wherein:
   said manual drive means is provided at least partially within said housing.

3. An endodontic handpiece according to claim 1, wherein:
   said drive member is generally cylindrical in shape.

4. An endodontic handpiece according to claim 3, wherein:
   said finger engagement means is a knurled pattern on an outer surface of said generally cylindrical member.

5. An endodontic handpiece according to claim 1, wherein:
   said tool engagement means is a first pinion gear having first teeth, and the engagement portion of the dental tool is a second pinion gear having second teeth able to mesh with said first teeth.

6. An endodontic handpiece according to claim 1, wherein:
   said tool engagement means is retractable from the engagement portion of the dental tool.

7. An endodontic handpiece according to claim 1, wherein:
   said manual drive member is distinct from said drive shaft.

8. An endodontic handpiece for rotating a dental tool about a dental tool longitudinal axis, the dental tool having an engagement portion, said endodontic handpiece comprising:
   a) a housing having a first end including an angle head, a second end, an interior, and a longitudinal axis, said angle head having an opening angled relative to said longitudinal axis of said housing, and sized to receive the engagement portion of the dental tool;
   b) tool engagement means for engaging the engagement portion of the dental tool, said engagement means extending into said opening of said angle head of said housing;
   c) shaft means for rotating said engagement means, said shaft means having a rotational axis substantially parallel to said longitudinal axis;
   d) driver means for rotating said shaft about said rotational axis of said drive shaft means; and
   e) spring-biased retraction means coupled to said tool engagement means for proximally retracting said tool engagement means out of engagement with the engagement portion of the dental tool,
   wherein when said shaft means is rotated about said rotational axis of said shaft means, the dental tool received in said opening and having its engagement portion engaged by said tool engagement means is rotated about the dental tool rotational axis.

9. An endodontic handpiece according to claim 8, further comprising:
   f) means for urging said shaft means and said driver means away form each other.

10. An endodontic handpiece according to claim 9, wherein:
    said shaft means has a distal end provided with a bore having a first non-circular cross-section, said driver means includes an axle portion having an rotational axis and a proximal end sized to be received in said bore of said shaft means and provided with a second non-circular cross-section rotationally interfering with said first non-circular cross-section, such that when said axle is rotated about said axle rotational axis, said shaft means is rotated about said shaft rotational axis.

11. An endodontic handpiece according to claim 9, wherein:
    the tool engagement portion of the dental tool is first gear teeth and said engagement means includes second gear teeth that mesh with said first gear teeth.

12. An endodontic handpiece according to claim 8, wherein:
    said drive means includes a cylindrical portion having a peripheral slot, and said retraction means comprises a sliding button member having a catch portion seated in said slot and a finger engagement portion residing outside said housing, said sliding button member axially movable relative to said housing to thereby move said tool means coupled to said shaft means relative to said engagement portion of the dental tool.

13. An endodontic handpiece according to claim 12, wherein:
    said slot is an annular groove.

14. An endodontic handpiece according to claim 8, wherein:
    said drive means is manually powered by fingers of a dentist.

15. An endodontic handpiece holdable in a hand of a dentist and manually operable using a single hand, said endodontic handpiece comprising:
    a) a housing having angle head and a longitudinal axis, said angle head having an opening angled relative to said longitudinal axis of said housing;

b) a drive shaft extending at least partially through said housing, said drive shaft having first and second ends and a rotational axis substantially parallel to said longitudinal axis;

c) engagement means coupled to said first end of said drive shaft and extending into said opening of said angle head of said housing;

d) manual drive means for translating movement of at least one finger of the dentist into rotation of said drive shaft; and e) a dental tool received in said opening of said angle head said dental tool including i) an engagement portion having an upper base portion having a first diameter, a lower base portion having a second diameter substantially the same as said first diameter, a central portion having a third diameter smaller than said first diameter, said central portion located between said upper and lower base portions and provided with gear teeth which abut said upper base portion, and ii) and tooling means coupled to said lower base portion for performing a dental procedure, wherein said engagement means is for engaging said engagement portion of said dental tool and when said drive shaft is rotated about said rotational axis of said drive shaft, said dental tool is rotated about said dental tool rotational axis.

16. An endodontic handpiece and dental tool assembly according to claim 20, wherein:

said engagement means of said endodontic handpiece is a pinion gear having a diameter, and said central portion of said head of said dental tool has a length substantially equal to said diameter of said pinion gear.

17. An endodontic handpiece and dental tool assembly according to claim 15, wherein:

said upper base of said dental tool is provided with an axial bore, and said angle head of housing is provided with a pin portion that extends into said bore.

18. An endodontic handpiece according to claim 15, wherein:

said housing is comprised of at least two components which are removably coupled to each other, such that said at least two components may be separated from each other to provide access to said interior of said housing.

\* \* \* \* \*